(12) United States Patent
Grenander

(10) Patent No.: US 9,072,595 B2
(45) Date of Patent: Jul. 7, 2015

(54) NECK RELIEF DEVICE, AND PIECE OF HEADGEAR INTENDED THEREFORE

(75) Inventor: Lars Grenander, Mellerud (SE)

(73) Assignee: LG SPINE-BAND AB, Mellerud (SE)

( * ) Notice: Subject to any disclaimer, the term of this patent is extended or adjusted under 35 U.S.C. 154(b) by 0 days.

(21) Appl. No.: 13/992,277

(22) PCT Filed: Nov. 24, 2011

(86) PCT No.: PCT/SE2011/051421
§ 371 (c)(1),
(2), (4) Date: Jun. 7, 2013

(87) PCT Pub. No.: WO2012/078094
PCT Pub. Date: Jun. 14, 2012

(65) Prior Publication Data
US 2013/0261520 A1    Oct. 3, 2013

(30) Foreign Application Priority Data
Dec. 8, 2010    (SE) ...................................... 1051296

(51) Int. Cl.
*A61F 5/00*    (2006.01)
*A61F 5/058*    (2006.01)
(Continued)

(52) U.S. Cl.
CPC ............ *A61F 5/05883* (2013.01); *A61F 5/055* (2013.01); *A61F 5/058* (2013.01); *A61F 5/37* (2013.01)

(58) Field of Classification Search
CPC ..... A61F 5/026; A61F 5/055; A61F 5/05883; A61F 5/013; A61F 5/05841; A61F 5/37; A61F 5/373; A61F 5/3753; A61F 13/0273; A61F 13/49007; A61F 2007/0001; A61F 2007/023; A61F 5/0046; A61F 5/028; A61F 5/03; A61F 9/026; A61F 13/145; A61F 2005/0176; A61F 2013/15016; A61F 5/0102; A61F 5/0123; A61F 5/05808; A61F 5/34; A61F 13/143; A61F 13/148; A61F 5/0113; A61F 5/024; A61F 5/445; A41C 1/10; A41C 3/00; A41C 1/08; A41C 1/00; A41C 1/02; A41C 1/06; A63B 21/0552; A63B 21/0442; A63B 2208/0252; A63B 21/0004; A63B 21/0555; A63B 21/1419; A63B 21/143; A63B 21/0428; A63B 21/0557; A63B 21/1415; A63B 2208/0204; A63B 23/0405; A63B 1/00
USPC ............................... 602/17–19; 2/45; 128/857
See application file for complete search history.

(56) References Cited

U.S. PATENT DOCUMENTS

| | | | | |
|---|---|---|---|---|
| 443,764 | A | * | 12/1890 | Hilliard ............................ 602/19 |
| 1,050,257 | A | * | 1/1913 | Trigg .................................. 2/45 |

(Continued)

FOREIGN PATENT DOCUMENTS

GB    2450960 A    1/2009

OTHER PUBLICATIONS

International Search Report and Written Opinion for PCT/SE2011/051421 dated Mar. 12, 2012, pp. 1-7.
(Continued)

*Primary Examiner* — Michael Brown
(74) *Attorney, Agent, or Firm* — John M. Harrington, Esq.; Johnson, Marcou & Isaacs, LLC

(57) ABSTRACT

The present invention relates to a neck relief device (1) comprising a flexible connecting device (3), which extends along the spine between an upper fixing point (3') above the cervical vertebrae (3A) of the spine and a lower fixing point (3D) below the cervical vertebrae (3A) of the spine, and a piece of headgear (20, 21) intended therefore.

20 Claims, 2 Drawing Sheets

(51) Int. Cl.
*A61F 5/055* (2006.01)
*A61F 5/37* (2006.01)

(56) References Cited

U.S. PATENT DOCUMENTS

| | | | | |
|---|---|---|---|---|
| 2,601,362 A | * | 6/1952 | Bowers | 2/8.1 |
| 2,828,737 A | * | 4/1958 | Hale | 602/19 |
| 2,845,926 A | * | 8/1958 | Hill | 128/206.17 |
| 3,738,654 A | * | 6/1973 | Whaley, Jr. | 473/438 |
| 5,521,653 A | * | 5/1996 | Anderson | 351/45 |
| 6,886,186 B2 | | 5/2005 | Jansen | |
| 2004/0068779 A1 | | 4/2004 | Duffy | |
| 2008/0139984 A1 | * | 6/2008 | Tranfic | 602/18 |
| 2010/0204628 A1 | | 8/2010 | Ghajar | |
| 2013/0296756 A1 | * | 11/2013 | Troncoso | 602/19 |

OTHER PUBLICATIONS

Chinese Office Action for co-pending Chinese Patent Application No. 201180058619.2 dated Nov. 3, 2014, pp. 1-6 (includes English translation).

* cited by examiner

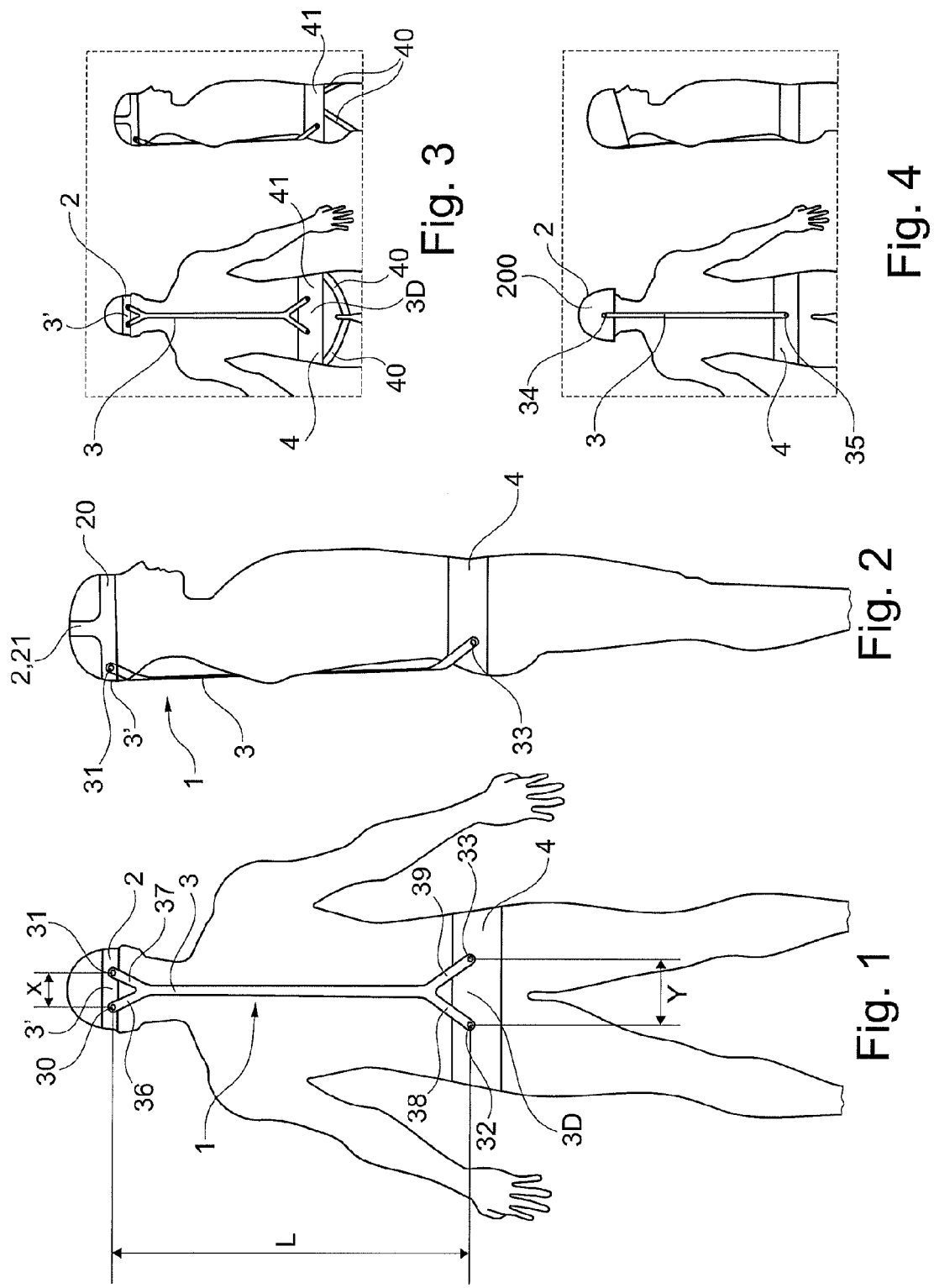

NECK RELIEF DEVICE, AND PIECE OF HEADGEAR INTENDED THEREFORE

CROSS-REFERENCE TO RELATED APPLICATIONS

This application is a 35 U.S.C. §371 national stage application of International Patent Application No. PCT/SE2011/051421 filed on Nov. 24, 2011, which claims the benefit of priority to Swedish Patent Application No. 1051296.0 filed on Dec. 8, 2010, the disclosures of which are hereby incorporated by reference.

TECHNICAL FIELD

The present invention relates to a neck relief device, and a piece of headgear intended therefore.

STATE OF THE ART

In today's society with a lot of sedentary jobs and repetitive static tasks, problems of the movement apparatus, and particularly of the shoulders and neck, are very common. Occupational groups like e.g. welders, healthcare staff, dentists, computer users and laboratory staff do a lot of work with the head bent forward, which causes a heavy strain on the neck. The direct and indirect costs arising in connection with problems of the movement apparatus are enormous.

A device for training and correcting the posture by means of attaching a rod along the back between head and waist, which is supposed to encourage the wearer of the device to tighten the abdominal muscles and press the back and head against the rod, is previously known from U.S. Pat. No. 5,199,940.

A similar device is previously known from CN 2642268, which discloses a device for preventing stooping of the back and leaning forward of the head when sitting down. The device comprises a vertically adjustable rod intended to be placed along the back, a waist belt for fixing the rod in place, shoulder straps, and straps to be fixed around the head which are attached to the rod.

Another body posture aid is disclosed in the document GB 2465424. A belt is fastened around the lower back. A vertically adjustable stick, extending along the spine all the way up to the head, is fixed to the back of the belt and intended to help the user keep in mind that certain parts of the back should be in contact with the stick, and to adopt a better posture in this way.

The document WO 2010/058046 discloses a harness, which is supposed to prevent pain in the lower back. The harness parts around the legs are attached to the shoulder parts via elastic bands, causing the harness to act as a spring.

BRIEF SUMMARY OF THE INVENTION

It is an object of the present invention to eliminate, or at least minimize the above-mentioned problems, which is achieved by means of a neck relief device comprising a flexible connecting device, which extends along the spine between an upper fixing point above the cervical vertebrae of the spine and a lower fixing point below the cervical vertebrae of the spine. Thanks to the invention, an ergonomic aid/training tool can be provided that reduces the torque resulting from the centre of gravity of the head, wherein the neck muscles are relieved.

Since the neck relief device comprises a connecting device that is at least partially elastic, an action of force is obtained that redistributes the pattern of activation to the throat muscles and increases the endurance of the deep neck flexors.

Since the connecting device, or its elastic portion, is replaceably disposed between an upper and a lower fixing point, a further advantage is obtained in that the elasticity of the neck relief device can be adapted to the needs of different persons. This advantage is also achieved in an embodiment where a non-elastic portion of the connecting device, having a first length, is replaceable with another non-elastic portion, having a second length, and/or is replaceable with another elastic portion.

According to one aspect of the invention, it is advantageous if the neck relief device comprises an upper fixing device, comprising a piece of headgear having an upper attachment for the connecting device, wherein said attachment is located on a level with or above the externus occipitalis protuberance, a bone protuberance on the occipital bone (the base of the skull), suitably adjacent to the base of the skull, to obtain the optimum biomechanical effect.

Since the upper fixing device comprises a forehead band, extending around the head and comprising said attachment, wherein said forehead band is elastic or otherwise adjustable in circumference, a very simple but sturdy design is provided, and also it becomes easy to remove and put on the neck relief device.

Further advantages are achieved if the neck relief device comprises a lower fixing device, comprising a girdle or belt provided with a lower attachment for the connecting device adjacent to the lower fixing point, on a level with the lower back adjacent to the sacrum, during use.

Since the girdle/belt comprises at least one fixing device, e.g. straps, extending between the front side and back side of the belt/girdle via the crotch, the advantage is achieved that the girdle/belt can be fixed vertically.

A simple and flexible fixing is achieved in that the connecting device comprises paired fastening means, interacting with said attachments, for example button and button hole, snap button, eye and hook, hook and loop, velcro straps.

According to one aspect of the invention, it applies that the neck relief device comprises a connecting device extending along the entire length of the spine, which also provides a stimulus to maintain the natural configuration of the spine.

BRIEF DESCRIPTION OF THE FIGURES

In the following, the invention will be described in greater detail with reference to the accompanying figures of the drawings, in which:

FIG. 1 shows a view from behind of a person using a neck relief device in a preferred embodiment of the invention;

FIG. 2 shows a view from the side of a person using the neck relief device;

FIG. 3 shows an alternative embodiment of the neck relief device according to the invention, as seen in a view from behind and in a side view;

FIG. 4 shows another alternative embodiment of the neck relief device according to the invention, as seen in a view from behind and in a side view;

DETAILED DESCRIPTION OF THE FIGURES

FIG. 1 shows a preferred embodiment of a neck relief device 1 according to the invention during use, that is to say secured along the back of a person between an upper fixing point 3' on the head and a lower fixing point 3D on a level with the lower back. The neck relief device 1 comprises an upper fixing device 2, a lower fixing device 4, and a connecting device 3 extending therebetween.

Figure 9:
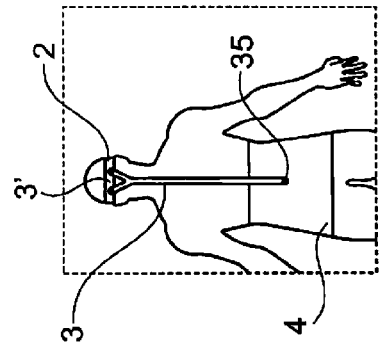
FIG. 9 shows a view from behind a person using neck relief device in an alternative embodiment of the invention.

In its simplest form, the neck relief device comprises an upper fixing device 2 in the form of a piece of headgear, which consists of a forehead band 20 extending around the head on a level with or above the externus occipitalis protuberance, a bone protuberance on the occipital bone (the base of the skull). The lower fixing device 4 comprises a belt 4 that is disposed around the torso on a level with the sacrum 3D. Most simply, the connecting device 3 comprises an elastic band attached between these two parts. In the continued description of the preferred embodiment of the lower fixing device 4, it is referred to as a belt, but it should be understood that other devices suitable for the purpose are also included, such as a girdle, as shown in FIG. 9, or a harness.

In the preferred embodiment, the piece of headgear also comprises a crown portion 21 (see FIG. 2), extending across the head from ear to ear and connecting the cheek pieces of the forehead band. The forehead band 20 and the crown portion 21 are thus continuous and form a helmet-like structure. The upper fixing device 2 is preferably made of a soft, slightly elastic material, and is available in different designs to fit different head shapes. At the back of the upper fixing device 2, there is an upper attachment 30, 31, preferably in the form of one or two buttons intended for attaching the elastic band 3 to the upper fixing device 2. If the fastening device comprises a button, it is suitably positioned centrally at the back of the headgear, in the extension of the neck. If the fastening device comprises two buttons, the buttons 30, 31 are spaced apart by a gap X in the range of 3-22 cm, more preferably 5-15 cm. These buttons 30, 31 allows the elastic band 3 to be easily attached and detached.

In the preferred embodiment, the belt 4 is preferably adapted to be closed by velcro straps, so that the belt 4 easily can be fastened around the body. At the back of the belt 4, there is a lower attachment 32, 33, preferably in the form of two buttons spaced apart by a gap Y in the range of 5-40 cm, more preferably 10-20 cm. The belt 4 is made of a material having some elasticity, so that the belt 4 can be fastened properly around the lumbar curve area on a level with the lower fixing point 3D (see FIG. 5).

The connecting device 3 comprises an elastic band which most simply has been slit at both of its ends, so that the ends assume the shape of a V. The band 3 thus comprises two upper fastening portions 36, 37 and two lower fastening portions 38, 39. Fastening means are disposed on said upper 36, 37 and lower fastening portions 38, 39, in this case button holes intended for attaching the band 3 to the buttons 30, 31, 32, 33 of the upper fixing device 2 and the lower fixing device 4, respectively. The elastic band 3 has a length L in the range of 20-150 cm, more preferably 60-120 cm.

Figure 5:
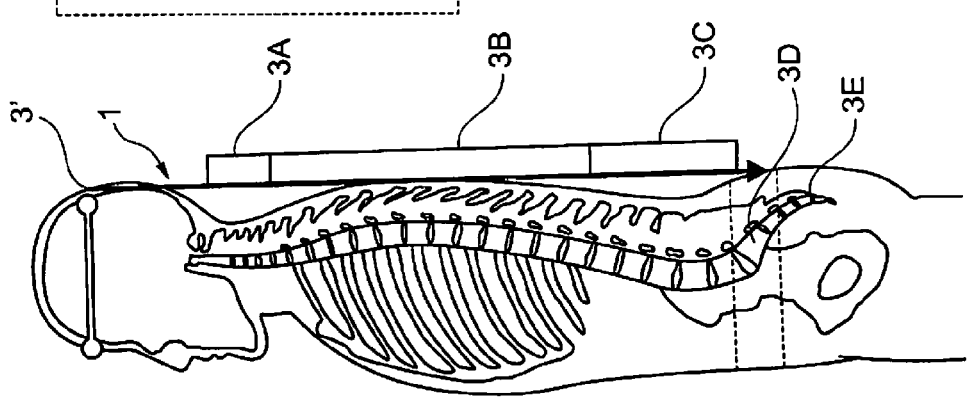
FIG. 5 shows a schematic profile view of the skeleton of a person carrying the neck relief device.

FIG. 2 shows the neck relief device 1 according to the invention in a side view, where it can be seen how the band 3 extends behind the entire length of the spine 3A, 3B, 3C, 3D, 3E (see FIG. 5). When using the neck relief device 1, the upper fixing device 2 is placed on the head of an individual, the lower fixing device 4 is fastened tightly around the body of the individual, preferably on a level with the lower back 3D. The elastic band 3 extends between these fixing devices 2, 4.

Figure 6:
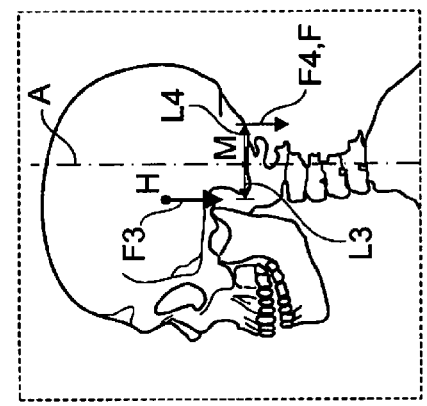
FIG. 6 shows schematically by force arrows how the centre of gravity of the head and the neck muscles act in an upright position.

In a fully upright standing or sitting position, the centre of gravity H of the head is located a few centimeters in front of a frontal axis of movement which, on the whole, can be regarded as passing through the ear canal, see FIG. 6. The position of the centre of gravity H in front of the axis of movement causes a natural forward torque that tends to tilt the head forward. This means that the postural neck muscles F, in particular the trapezius muscle and the underlying shorter cervical muscles, have to be activated continuously to prevent a forward tilting of the head. By the expression natural forward torque is meant the forward tilting torque caused by the head's weight in an upright position. The forward tilting torque increases during tasks where positions with the neck bent forward are required, since the centre of gravity H is moved further forward (further away from the axis of movement), see FIG. 7. The resulting torque increases even more when working with work headgear, e.g. a safety helmet and visor. Thereby, the neck muscles F, see FIG. 6, have to activated to a greater extent, with the risk of fatigue, symptoms of overload, pain, and work injuries.

Figure 8:
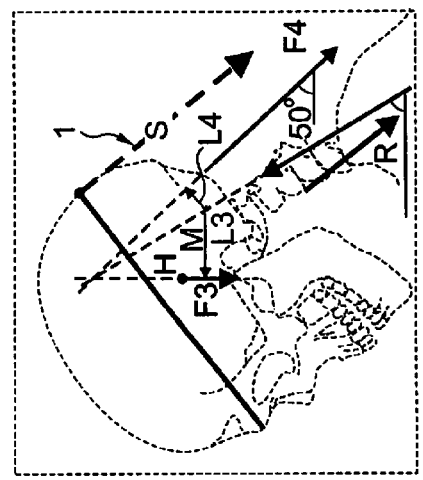
FIG. 8 shows schematically by force arrows how the centre of gravity of the head, the neck muscles, the throat muscles, and the neck relief device act during forward bending

The neck relief device 1 according to the invention reduces the resulting torque by an opposing force S, acting in parallel with the force of action F4 of the neck muscles, see FIG. 8, on the opposite side of the axis of movement. In that way, the neck muscles F are activated to a smaller extent. In a preferred embodiment, the neck relief device 1 also causes a redistribution of the activation pattern around the neck by applying a pull/torque S (backward) in the neck relief device 1 which exceeds the natural forward torque of the head in the upright position thereby resulting in an activation of the nodding muscles R of the throat, mainly the sternocleidomastoid muscle, instead of the neck muscles F in order to balance the head. In a forward bent position the neck relief device 1 is further arranged to apply a pull/torque S which preferably exceeds the resulting torque in the forward bent position, as illustrated in FIG. 4. In this way, the muscle activation is redistributed and can reduce the tension level and pain conditions at the back of the neck. By activating the nodding muscles, also another physiological effect, called "antagonist inhibition/reciprocal inhibition", is achieved. This means that by activating the muscles of the opposite side of the neck joint, in this case the throat muscles R, a direct reflexive inhibition of the extent of activation in the neck muscles F is obtained since they cannot be activated simultaneously. Nerve impulses to the neck muscles are consequently blocked by the activity of the nodding muscles pressing the head forward and the neck muscles become completely relaxed. Recent research directed toward neck pain has found a high level of evidence that endurance training of deep neck flexors results in effects such as, inter alia, increased muscle strength, reduced pain and reduced headaches. Thanks to the present neck relief device 1, the load on the neck muscles F can be reduced and problems in the neck area be prevented, and be used for rehabilitating neck patients. Therefore, in a preferred embodiment, the elasticity is so adapted that the effect of "antagonist inhibition/reciprocal inhibition" is always achieved.

In static equilibrium around the upper neck joints, the following applies:

The forward torque (the weight of the head) should be equal to the backward bending moment (the activity of the muscles) about a fulcrum M.

Schematically:

$$F3 \times L3 = F4 \times L4$$

F3=the weight of the head
L3=the length of the moment arm by which the head acts in front of the axis of movement
F4=the force of the neck muscles
L4=the length of the moment arm by which the muscles act behind the axis of movement In FIG. 8, the forward torque results from the weight of the head (H) acting with a certain length (L3) in front of the axis of movement. The forward bending moment (without a helmet) is H×L3, where H is the mass of the head that is equal to 5% of the body weight x the force of gravity. The backward bending moment is F4×L4, where F4 represents the resulting muscle force, and which the neck relief device (S) seeks to reduce/nullify.
Accordingly:

$$H \times L3 = F4 \times L4 \quad F4 = (H \times L3)/L4$$

Example calculation, calculation of muscle activity F4:

$$((0.05 \times \text{the body weight in kg} \times 9.82) \times 0.02 \text{ m})/0.04 \text{ m}$$

If the body weight of the person is 80 kg, the muscle activity in the above example becomes $$((0.05 \times 80 \times 9.82) \times 0.02)/0.04 = 19.64 \text{ N}$$

This activity increases rapidly with helmet use (additional weight) and with increased forward bending angle. The neck relief device seeks to replace this resulting muscle force, or even to exceed this force, so that the throat muscles (R) are engaged in order to maintain static equilibrium and cause a reciprocal inhibition of the neck muscles.

Hitherto, only the biomechanical forces around the upper neck joints have been described. The corresponding calculation can be performed for the entire neck, if an axis of movement around the 7:th cervical vertebra is assumed. Also the weight of the cervical spine region (approx. 2% of the body weight) has to be included in that case. In this case, the forces on the neck/shoulder muscles will become even greater.

In the preferred embodiment, the neck relief device 1 also provides a stimulus to maintain the natural configuration of the back, which assumes an S-shape as viewed from the side. The lumbar curve is convex forward, the thoracic spine is convex backward, and the cervical spine is convex forward, see FIG. 5. The spine is most effective in carrying loads if the S-shape can be maintained. The neck relief device 1 provides afferent impulses to the brain, stimulating a more upright posture and thus maintained natural curvatures. If the S-shape is maintained, the resulting shear forces between the vertebrae, which otherwise could lead to overload injuries, are minimized.

FIG. 3 shows an alternative embodiment of the lower fixing device 4, in the form of a harness, comprising a belt 41 and at least one third fixing device, here in the form of a pair of straps 40. The straps 40 are fixedly disposed on the front side of the belt 41 and extend inward/downward toward the groins, via the crotch further around the thighs, below the behind and upward toward the belt 41 again at the outside of the thighs. Preferably, both the belt 41 and the straps 40 are made of an elastic material, so that it is possible to step into the harness and pull it into place, so that the belt 41 is positioned around the lower back and the straps 40 around the thighs and below the buttocks. An advantage of this embodiment is that the fixing point in the lumbar curve area is held still against the upper part of the sacrum below the lumbar spine curve. In order to achieve the best possible effect of the neck relief device 1, both fixing points 3', 3D should be fixed. The upper fixing point 3' should be on a level with or above the externus occipitalis protuberance (a bone protuberance) on the occipital bone (the base of the skull) and/or above the superior nuchal line. The advantage of having the fixing point 3' positioned above these areas is that the neck relief device 1 will thus get the longest possible moment arm, resulting in the best possible effect of the neck relief device 1. It is conceivable to further increase the length of the moment arm by arranging the fixing point 3' a short distance outside the skull, typically 2-5 cm, by arranging e.g. a pin having fixing means at its distal end. If the fixing point 3' is positioned below these areas, the moment arm is reduced and the effect of the neck relief device 1 decreases, but experiences have shown that some effect still can be achieved, that being the reason why it will be appreciated that the purpose of the invention can still be achieved with an embodiment where the fixing point 3' is allowed a certain displacement, either due to the design of the piece of headgear or due to the fact that the piece of headgear is allowed a certain mobility on the head during use. The elastic band 3 extends from the fixing point 3' in parallel with the median nuchal line down toward the spine, and the lower fixing point 3D should be fixed relative to the sacrum 3D to produce the right effect on the lumbar spine lordosis (the lumbar curve). The elasticity in the band 3 should be adjustable, for example by having a differently strong elasticity of different bands 3, to achieve the maximum tension relief sensation. The adjustability is also important when the neck relief device 1 is used as a training tool requiring an adjustable load level.

FIG. 4 shows another alternative embodiment of the neck relief device 1 according to the invention. In this embodiment, the upper fixing device 2 comprises a helmet 200. The lower fixing device 4 comprises a belt 4 as above. In this embodiment, the elastic band 3 comprises a straight band having a fastening device 34 disposed at its upper end, preferably a button hole 34, which is intended to be attached to the helmet 200.

The neck relief device 1 according to the invention is also intended to be usable for occupational groups where some kind of headgear is worn, e.g. a welding helmet. The neck relief device 1 is then preferably attached via a button hole 34 in its upper end, which is slipped over an attachment at the back of the lower edge of the helmet, e.g. the already existing screw head that is usually present at the back of e.g. a welding helmet for adjusting the circumference of the helmet. When used in connection with e.g. a welding helmet, the lower fixing device 4 can consist of one of the embodiments above, alternatively the elastic band 3 can be attached to e.g. a protective overall, via a button disposed at the back of said overall.

FIG. 5 shows how the neck relief device 1, in a preferred embodiment, extends between the upper fixing point 3' and the lower fixing point 3D.

FIG. 6 shows schematically how the centre of gravity H of the head and the neck muscles F act in an upright position. The head would tilt forward if the neck muscles F were not activated to counteract the natural forward torque caused by the centre of gravity H. The dashed line A schematically indicates an axis of movement.

Figure 7:
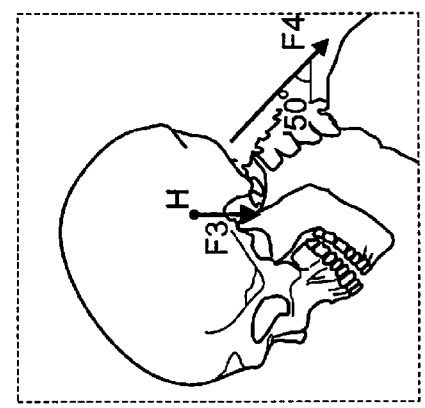
FIG. 7 shows schematically by force arrows how the centre of gravity of the head and the neck muscles act during forward bending.

FIG. 7 shows schematically how the centre of gravity H of the head is moved further away from the axis of movement during forward bending, resulting in a larger torque that the neck muscles F have to counteract.

FIG. 8 schematically shows how the action/pull/force S of the neck relief device 1 acts in parallel with the force of action F4 of the neck muscles and therefore has a relieving effect on the neck muscles F. If the elastic force in the neck relief device 1 exceeds the forward tilting torque H of the head, the throat muscles R on the front side are activated in order to balance the head. This causes a reciprocal inhibition (suppression, tension relief) of the heavily loaded neck muscles F.

The neck relief device 1 according to the invention has several fields of application:
- in the working life of occupational groups who do a lot of work with the head bent forward, such as welders, dentists, computer users, and others.
- in fitness activities, where the neck relief device 1 is perfectly combinable with gardening, walks and Nordic walking, for optimizing the training effect and for stimulating the posture.
- in rehabilitation activities as a training tool, e.g. for physiotherapists, chiropractors and naprapaths, for cervical endurance training and specific training of deep neck flexors.

ALTERNATIVE EMBODIMENTS

The invention is not limited by what has been described hereinabove, but can be varied within the scope of the following claims. For instance, it will be appreciated that the connecting device may assume different embodiments, e.g. have a width that is substantially larger than the thickness, or have a circular cross-section.

Instead of having different elasticity of different bands for replacement, the elasticity of a band can be adjusted in that the connecting device has several fastening devices positioned at a gradually increasing distance from the end of the connecting device, e.g. several button holes in a row, so that the fastening device thus can be selected according to the desired elasticity.

The connecting device can also comprise several parts, where e.g. the parts attached to the upper and lower fixing devices consist of non-elastic portions, and an elastic portion is disposed therebetween. The connecting device can, of course, comprise other combinations of elastic and non-elastic portions than the one mentioned here, which portions can be mutually replaceable to thereby produce a number of different combinations with different elasticity, length, etc. A non-elastic portion of the connecting device, having a first length (L1), can e.g. be replaceable with another non-elastic portion, having a second length (L2), and/or be replaceable with another elastic portion. The connecting device could also comprise more than one elastic band, e.g. two bands positioned on each side of the spine and which can have different elasticities, for exercising the muscles on one side of the body of a person with a twisted spine as a result of uneven loading.

Within the scope of the inventive concept, it will be appreciated that the action of force desired from the connecting device can also be achieved by means of different spring devices.

An embodiment that does not encompass the whole back is also conceivable. The connecting device can extend from the base of the skull along the spine to below the cervical vertebrae and be attached there, for example to an elastic belt that is fastened around the chest below the arm pits, still another alternative could be to have a harness into which the arms are slipped, to thus hold the band in place along the spine.

The connecting device can be attached to the fixing devices in other ways than in the described embodiment with cooperating buttons and button holes. Other interacting, paired fastening means, e.g. snap buttons, eye and hook, hook and loop, velcro straps, are of course conceivable, as well as suspender fasteners or other clip attachments. Another alternative is to sew, glue or rivet the band to the fixing devices when the neck relief device is fitted.

Within the scope of the invention, it will be appreciated that the piece of headgear does not have to be made from an elastic material. For example, the interior lining of a construction/welding helmet, broadly resembling the embodiment shown in FIG. 2 but made in plastic, can be used. The interior lining has a means of adjustment suitable for the purpose of adaptation to different head sizes, in the form of an adjustment device on the neck portion of the interior lining. Furthermore, there is a possibility to use the adjustment screw that the adjustment device comprises as an attachment for the connecting device. A separate attachment is, of course, also conceivable, and the attachment can be located in a suitable position from a structural point of view, to facilitate the attachment of the connecting device and to allow integration of the interior lining into a helmet. The attachment can thus be placed in the area at the back of the head up to the top of the crown, and be slid backward, downward, for example in a groove or a channel. Preferably, the attachment is easily accessible on the outside of the helmet, or on its inside, and, as previously described, the attachment can, for example, consist of one or several buttons, loops or eyes for a hook or screws. Preferably, the connecting device extends freely from a point on a level with or above the externus occipitalis protuberance (a bone protuberance) on the occipital bone (the base of the skull) and/or above the superior nuchal line.

A conventional cap/hat, where a fastening device for the band is disposed at the back, can be used as the upper fixing device. It will also be appreciated that the connecting device can be equipped at both of its ends with e.g. an openable hook, which simply hooks into a loop on a pair of trousers or another suitable fastening device.

The skilled person will also appreciate that the neck relief device can be integrated into the working clothes when the neck relief device is used in certain occupational categories where different kinds of protective equipment are used. If, for example, a helmet is used, the connecting device can be attached at the back to existing screws/buttons, or the manufacturers can adapt the helmet for users of the neck relief device.

The same applies to e.g. overalls/work trousers, where the manufacturers through cooperation can provide a fastening device at the back, alternatively a belt adapted for attaching the connecting device thereto can be provided.

The materials in the different fixing devices can of course vary, without departing from the purpose of holding the band in place.

Furthermore, it will be appreciated that the parts included in the device are not limited solely to use together with each other, as has been exemplified in the description. It should be understood that they can be used separately in applications for which they are suited and that, in addition to the tangible examples given here, other aspects of the devices according to the invention could form the basis of independent claims related to separate devices, or use together with anyone or any of other described devices. For instance, it will be appreciated that different types of headgear or lower fixing devices which have been designed for facilitating the use of a connecting device according to the invention for specific occupational categories should be encompassed by the inventive concept.

The invention claimed is:

1. A neck relief device for deactivating the neck muscles of a user by inducing activation of the throat muscles of the user, the neck relief device, comprising:

an upper fixing device configured to be attached to the head of the user;

a lower fixing device configured to be attached to a lower fixing point below the cervical vertebrae of the spine of the user;

a flexible connecting device fastened directly to the upper and lower fixing devices via first and second attaching means, respectively, and connecting the upper and lower fixing devices, the flexible connecting device comprising at least one of an elastic band and a spring; and the flexible connecting device having an elasticity continuously exerting a tensile force (S) between the attached upper and lower fixing devices in a direction parallel with a force of action (F4) of the user's neck muscles, the continuously exerted tensile force (S) exceeding a natural forward torque of the user's head over a range of head angles varying from an upright position of the user's head to a forward tilted position of the user's head.

2. The neck relief device according to claim 1, wherein said at least one of the elastic band and the spring is replaceable.

3. The neck relief device according to claim 1, wherein said first attaching means comprises an upper attachment configured to be attached to the upper fixing device at different locations on the upper fixing device.

4. The neck relief device according to claim 3, further comprising a non-elastic portion of the connecting device having a first length (L1), that is replaceable with at least one of:

another non-elastic portion, having a second length (L2), and another at least one of an elastic band and a spring.

5. The neck relief device according to claim 3, wherein the upper fixing device comprises a piece of headgear, and said upper attachment is configured to be attached to the head on a level with or above the superior nuchal line.

6. The neck relief device according to claim 5, wherein the upper attachment is configured to be attached to a level with or above the externus occipitalis protuberance.

7. The neck relief device according to claim 5, wherein the piece of headgear comprises a forehead band extending around the head, and wherein said forehead band is elastic or otherwise adjustable in circumference.

8. The neck relief device according to claim 1, wherein the lower fixing device comprises at least one of a girdle and a belt.

9. A neck relief device for deactivating the neck muscles of a user by inducing activation of the throat muscles of the user, the neck relief device, comprising:

an upper fixing device configured to be attached to the head of the user:

a lower fixing device configured to be attached to a lower fixing point below the cervical vertebrae of the spine of the user;

a flexible connecting device connecting the upper and lower fixing devices, the flexible connecting device comprising at least one of an elastic band and a spring;

the flexible connecting device having an elasticity continuously exerting a tensile force (S) between the attached upper and lower fixing devices in a direction parallel with a force of action (F4) of the user's neck muscles, the continuously exerted tensile force (S) exceeding a natural forward torque of the user's head over a range of head angles varying from an upright position of the user's head to a forward tilted position of the user's head; and wherein the lower fixing device comprises at least one of a pair of overalls, and a pair of trousers, a girdle, and a belt.

10. The neck relief device according to claim 9, further comprising a lower attachment is adjacent to the sacrum.

11. The neck relief device according to claim 8, wherein the at least one of a girdle and a belt comprises at least one third fixing device extending between a front side and a back side of the at least one of the girdle and the belt via the crotch of the user.

12. The neck relief device according to claim 5, wherein said upper and lower attaching means, respectively, interact with said connecting device.

13. A device comprising:

a piece of headgear having upper attachment means for a flexible connecting device, wherein said piece of headgear is configured to be attached to the head of a user on a level with or above the superior nuchal line, the piece of headgear comprising a circumferential portion extending around the head and a crown portion connected thereto, said crown portion extending across the head;

a lower fixing device configured to be attached to the user at a point below the cervical vertebrae of the spine of the user; and the flexible connecting device being fastened directly to the piece of headgear via the upper attachment means and directly to the lower fixing device via lower attachment means, and the flexible connecting device comprising at least one of an elastic band and a spring.

14. The device according to claim 13, wherein the upper attachment is located on a level with or above the externus occipitalis protuberance.

15. The device according to claim 13, wherein the piece of headgear comprises a forehead band extending around the head, wherein said forehead band is elastic or otherwise adjustable in circumference.

16. The device according to claim 13, wherein said upper attachment means forms an integrated part of the piece of headgear, and is so adapted that the connecting device easily can be attached and detached while the piece of headgear is on the head of the user.

17. The neck relief device of claim 1, wherein the upper fixing device comprises a helmet.

18. The neck relief device of claim 17, further comprising a pin connected to the helmet that locates a connection between the pin and the flexible connecting device a distance 2-5 cm outside the skull.

19. The device of claim 13, wherein the upper attachment means comprises a pin that locates the upper attachment 2-5 cm outside the skull.

20. The neck relief device of claim 1, wherein the upper fixing device comprises a pin that locates a point of connection between the upper fixing device and the flexible connecting device a distance of 2-5 cm from the skull.

* * * * *

UNITED STATES PATENT AND TRADEMARK OFFICE
CERTIFICATE OF CORRECTION

| | | |
|---|---|---|
| PATENT NO. | : 9,072,595 B2 | Page 1 of 1 |
| APPLICATION NO. | : 13/992277 | |
| DATED | : July 7, 2015 | |
| INVENTOR(S) | : Lars Grenander | |

It is certified that error appears in the above-identified patent and that said Letters Patent is hereby corrected as shown below:

At Column 5, Line 19, after the first occurrence of "L4", change the mathematical symbol from "-" to - --> -;

At Column 10, Line 6, after "overalls", remove the word "and" before "a pair of trousers...";

At Column 10, Line 9, after "attachment", remove the word "is" before "adjacent";

At Column 10, Line 14, Claim 12, after "according to" change claim "5" to claim - 1 -.

Signed and Sealed this
Tenth Day of November, 2015

Michelle K. Lee
*Director of the United States Patent and Trademark Office*